United States Patent [19]

Morley

[11] 4,197,417
[45] Apr. 8, 1980

[54] PROCESS FOR THE MANUFACTURE OF O-BENZYL TOLUENES

[75] Inventor: John O. Morley, Dunblane, Scotland

[73] Assignee: Imperial Chemical Industries Limited, London, England

[21] Appl. No.: 939,913

[22] Filed: Sep. 5, 1978

[30] Foreign Application Priority Data

Sep. 28, 1977 [GB] United Kingdom .............. 40304/77

[51] Int. Cl.$^2$ .......................... C07C 15/18; C07C 3/52
[52] U.S. Cl. ...................................... 585/455; 585/467
[58] Field of Search .......................... 260/668 R, 668 B

[56] References Cited

U.S. PATENT DOCUMENTS 3,978,144  8/1976  Eilingsfeld et al. ............. 260/668 R Primary Examiner—George Crasanakis
Attorney, Agent, or Firm—Cushman, Darby & Cushman

[57] ABSTRACT

Manufacture of o-benzyltoluenes by reaction of a benzyl halide of formula

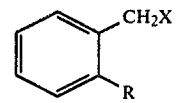

with a compound of formula

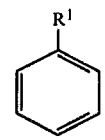

at 50° to 250° C., one of R and $R^1$ being methyl and the other H or methyl, and adding the compound II to a mixture of III with a small amount of iron or iron compound.

4 Claims, No Drawings

PROCESS FOR THE MANUFACTURE OF O-BENZYL TOLUENES

This invention relates to a new process for the manufacture of o-benzyl toluene and alkyl derivatives thereof.

Hitherto, o-benzyltoluenes have been prepared by: 1. the reaction of toluene or m- or p-xylene with benzyl chloride either in the presence of zinc dust (Ber., 1872,5,799; 1873,6,906) or beryllium chloride (Ber., 1939,72,1414); 2. the reaction of benzyl chloride either with toluene in the presence of metal oxides (Bull.Chem.Soc.Japan, 1975,48(10), 2944) and metal sulphates (Chem.Lett., 1974,929) or with m- or o-xylene with 10% by weight of aluminium chloride (based on the chloride) in very dilute solution (J.Amer.Chem.Soc., 1960,82,3653); 3. the reaction of α-chloro-o-xylene with benzene in the presence of zinc dust (Ber., 1874,7,1544).

All of these methods, however, are unsatisfactory because they are either carried out in very dilute solution or give poor yields of the required product or complex mixtures which are difficult to separate, e.g. benzylation of toluene under method (2) with zinc oxide gives 43% o-methyldiphenylmethane, 6% of m-methyldiphenylmethane and 51% of p-methyldiphenylmethane. The methods described, therefore, are unsuitable for industrial use.

The present invention provides a process for the manufacture of o-benzyltoluenes of the formula:

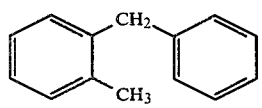

I wherein the benzene rings may be substituted by one or more alkyl groups, which comprises adding a benzyl halide compound of the formula:

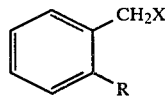

II wherein X is Cl, Br or I to a mixture of iron or an iron compound with a hydrocarbon compound of the formula:

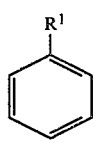

III at a temperature of 50° to 250° C., wherein one of R and $R^1$ is methyl and the other is H or methyl, and compounds II and III optionally being further substituted by one or more alkyl groups, preferably of at most 4 carbon atoms.

As examples of compounds of formula II there may be mentioned benzyl chloride, benzyl bromide, benzyl iodide, α-chloro-o-xylene and α-chloro-p-xylene.

As examples of compounds of formula III, there may be mentioned benzene, toluene, ethylbenzene, t-butylbenzene, o-, m- and p-xylenes, p-cymene and p-t-butyltoluene. When R in the compound of formula II is H, then that in the compound of formula III must be $CH_3$; it is preferred that in this situation, the compound of formula III contains a second substituent in m- or p-position to the methyl group.

The amount of hydrocarbon used can vary from one equivalent to the benzyl halide compound to a large excess.

The iron compound if used is preferably in the ferric state; metallic iron may be added as an alloy thereof. It is preferred to use iron itself, ferric chloride, ferric sulphate or ferric oxide. The amount of iron or iron compound used can vary from 0.001 to 0.5 part, preferably 0.005 to 0.05 part, by weight for each part by weight of the benzyl halide compound.

Under appropriate conditions, the reaction proceeds smoothly with evolution of hydrogen halide, the amount of polymeric material or other by products is small and the yield of the o-benzyltoluene compound is excellent. In some instances, however, especially when using iron oxide or iron sulphate, an induction period is found to occur; this situation can be overcome by including a small proportion, e.g. 1% to 5%, of the total amount of the benzyl halide to be used, in the heated mixture of hydrocarbon and iron or iron compound and allowing the reaction to commence before adding further amounts of the halide.

The product or products resulting from the reaction can be isolated from the mixture at the end of the reaction period by conventional distillation methods.

The invention is illustrated but not limited by the following examples in which the parts and percentages are by weight.

EXAMPLE 1

63.3 Parts of benzyl chloride at 20° are slowly added during 2 hours to a mixture of 1 part of iron (III) chloride and 531 parts of p-xylene held at a temperature of 115°–120° C. The rate of hydrogen chloride evolution is found to be directly proportional to the rate of benzyl chloride addition. After addition, the mixture is held at 120° C. for 3 hours then filtered to remove insoluble matter, and the unreacted p-xylene (406 parts) removed by atmospheric distillation at 135°–145° C. The residue is distilled under reduced pressure at 2–3 mm Hg and a further fraction of p-xylene (64 parts) is obtained at 30°–40° C. The total recovery of p-xylene is 470 parts (98% recovery). The product, 2,5-dimethyldiphenylmethane is obtained at 126°–134° C.: yield 80 parts (82% of theory). A residue of 10.1 parts of polymer remains after distillation.

EXAMPLE 2

The procedure of Example 1 is repeated except that 1 part of iron (III) sulphate is used in place of the chloride. This change results in an induction period of 10 minutes before hydrogen chloride evolution commences. After reaction and work-up as before there are obtained by atmospheric and vacuum distillation 472.5 parts of p-xylene (99% recovery), 76.5 parts of 2,5-dimethyldiphenylmethane (78% of theory), b.p. 126°–134° at 3 mm Hg. and 12.3 parts of residual polymer.

EXAMPLE 3

The procedure of Example 1 is repeated except that 537 parts of p-cymene are used in place of p-xylene, the benzyl chloride is added over 4 hours to the mixture of hydrocarbon and catalyst at 135° C., and reaction is continued for a further 2 hours at 135° C. and then 4 hours at 160° C. After reaction there are obtained by vacuum distillation at 3 mm Hg, 431.5 parts of p-cymene (92% recovery), b.p. 4°–56° C., and a mixture of 68.4 parts of 2-methyl-5-isopropyldiphenylmethane (61% of theory) and 24.6 parts of 5-methyl-2-isopropyldiphenylmethane (22% of theory), b.p. 140°–180° C., identified and estimated by nmr spectroscopy.

EXAMPLE 4

The procedure of Example 3 is repeated except that 370.6 parts of p-t-butyltoluene are used in place of p-cymene and the mixture is held at 160° C. for 2 hours only. After reaction and work-up there are obtained by vacuum distillation at 3 mm of Hg, 287.6 parts of p-t-butyltoluene (97% recovery), b.p. 55°–65° C., and 97.7 parts of 2-methyl-5-t-butyldiphenylmethane (82% theory) b.p. 160°–170° C.

EXAMPLE 5

70.3 Parts of α-chloro-p-xylene at 20° are slowly added during 2 hours to a mixture of 1 part of iron (III) chloride and 427.7 parts of m-xylene held at 130°–135° C. The mixture is held at this temperature for a further 3 hours and then worked up as before. After reaction there are obtained by vacuum distillation at 3 mm of Hg 344.3 parts of m-xylene (92% recovery) and a mixture of 62.8 parts of 2,4,4'-trimethyldiphenylmethane (60% of theory) with 12.1 parts of 2,4',6-trimethyldiphenylmethane (12% of theory), b.p. 140°–160° C., identified and estimated by n.m.r. spectroscopy.

EXAMPLE 6

The procedure of Example 1 is repeated except that 265.4 parts of m-xylene are used in place of p-xylene, 1 part of iron (III) oxide is used in place of the chloride, benzyl chloride is added over 3 hours at 125° C. and the mixture held for a further 1 hour at this temperature. After reaction and removal of catalyst by filtration and unreacted m-xylene by atmospheric distillation, there are obtained by vacuum distillation at 3 mm of Hg a mixture of 58.5 parts of 2,4-dimethyldiphenylmethane (60% of theory) with 15.5 parts of 2,6-dimethyldiphenylmethane (16% of theory), b.p. 129°–140° C., identified and estimated by n.m.r. spectroscopy.

EXAMPLE 7

The procedure of Example 1 is repeated except that 105.6 parts of benzyl chloride and 444 parts of p-xylene are used in the presence of 1 part of iron (III) oxide in place of the chloride. There is an induction period of 10 minutes before hydrogen chloride evolution commences. After reaction and work up there are obtained by atmospheric and vacuum distillation 353 parts of p-xylene (99% recovery), 115 parts of 2,5-dimethyldiphenylmethane (70% of theory), b.p. 128°–136° C. at 3 mm Hg, and 29.6 parts of residual polymer.

EXAMPLE 8

70.3 Parts of α-chloro-o-xylene at 20° C. are slowly added during 2 hours to a mixture of 0.5 part of iron (III) chloride and 780 parts of benzene at 70°–75° C. The mixture is refluxed for a further ½ hour and distilled at atmospheric pressure to give 729 parts of benzene (96% recovery). Vacuum distillation at 2 mm of Hg gives 37.3 parts of o-methyldiphenylmethane (41% of theory), b.p. 96°–98° C., 41 parts of polymer remains after distillation.

EXAMPLE 9

The procedure of Example 8 is repeated except that 623 parts of t-butylbenzene are used in place of benzene and the reaction is carried out with 1 part of iron (III) chloride at 115° C. After reaction, and removal of insolubles, there are obtained by vacuum distillation 543 parts of t-butylbenzene (98% recovery), 80.7 parts of 2-methyl-4'-t-butyldiphenylmethane (68% of theory), b.p. 140°–148° C., and 17.1 parts of residual polymer.

EXAMPLE 10

The procedure of Example 1 is repeated except that 0.5 part of iron (III) chloride is used as catalyst, the reaction is carried out at 95° C., and the holding time is 2 hours instead of 3 hours. After reaction, the liquors are analysed by g.l.c. and found to contain 83.4 parts of 2,5-dimethyldiphenylmethane (85% of theory). The product mixture is distilled at atmospheric pressure to remove 462 parts of p-xylene (97% recovery), b.p. 135°–145° C., and then at 3 mm of Hg to give 79.3 parts of isolated 2,5-dimethyldiphenylmethane (81% of theory), b.p. 126°–134° C., 12.8 parts of polymer remain after distillation.

EXAMPLE 11

The procedure of Example 10 is repeated except that the reaction is carried out at 85° with 1062 parts of p-xylene. After reaction the liquors are analysed by g.l.c. and found to contain 90.2 parts of 2,5-dimethyldiphenylmethane (92% of theory). The product mixture is distilled at atmospheric pressure to remove 990 parts of p-xylene (98% recovery), b.p. 135°–145° C., and then at 3 mm of Hg to give 85.3 parts of isolated 2,5-dimethyldiphenylmethane (87% of theory), b.p. 126°–134° C., 6.6 parts of polymer remain after distillation.

What we claim is:

1. A process for the manufacture of o-benzyltoluenes of the formula:

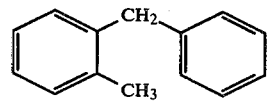

I wherein the benzene rings may be substituted by one or more alkyl groups, by reaction of a benzyl halide of the formula:

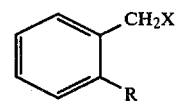

II and a compound of the formula:

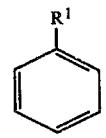

III wherein one of R and R¹ is methyl and the other is H or methyl and compounds II and III at a temperature of 50° to 250° C., said process being carried out by adding compound II to a mixture of the compound III and a catalytic amount of iron metal or an iron compound.

2. A process as claimed in claim 1, wherein the amount of iron or iron compound is from 0.005 to 0.05 part per part by weight of compound III.

3. A process as claimed in claim 1 or claim 2 wherein there is used metallic iron, ferric chloride, ferric sulphate or ferric oxide.

4. A process as claimed in claim 1, wherein said compound I and said compounds II and III are further substituted by one or more alkyl groups.

* * * * *